(12) United States Patent
Commandeur et al.

(10) Patent No.: US 6,265,628 B1
(45) Date of Patent: Jul. 24, 2001

(54) PROCESS FOR THE CONTINUOUS PREPARATION OF MONO- AND/OR BIS (MONO-AND/OR DI-AND/OR TRICHLOROMETHYL) BENZENES

(75) Inventors: Raymond Commandeur, Vizille; Régis Loze, Saint-Auban, both of (FR)

(73) Assignee: Elf Atochem, S.A. (FR)

( * ) Notice: Subject to any disclaimer, the term of this patent is extended or adjusted under 35 U.S.C. 154(b) by 0 days.

(21) Appl. No.: 09/288,675

(22) Filed: Apr. 9, 1999

(30) Foreign Application Priority Data

Apr. 9, 1998 (FR) .................................................. 98 04460

(51) Int. Cl.$^7$ .............................. C07C 17/00; C07C 22/00
(52) U.S. Cl. .................... 570/194; 570/182; 204/157.94; 204/157.99
(58) Field of Search ..................................... 570/182, 194; 204/157.94, 157.99

(56) References Cited

U.S. PATENT DOCUMENTS

| 2,810,688 | * | 10/1957 | Ivins et al. ........................... 204/163 |
| 4,056,455 | | 11/1977 | Rudolf et al. ........................ 204/163 |

FOREIGN PATENT DOCUMENTS

| 2156911 | | 6/1973 | (FR) . |
| 583634 | * | 12/1946 | (GB) . |
| 1401038 | | 7/1975 | (GB) . |

OTHER PUBLICATIONS

FR 2 156 911—English Abstract Jan. 6, 1973.

* cited by examiner

*Primary Examiner*—Edna Wong
(74) *Attorney, Agent, or Firm*—Millen, White, Zelano & Branigan, P.C.

(57) ABSTRACT

In a process for the continuous preparation of mono- and/or bis(mono- and/or di- and/or trichloromethyl) benzenes by gradual chlorination of the corresponding mono-or dimethylbenzenes in several reactors in cascade, the first reactor has a greater volume than each of the other reactors.

16 Claims, 2 Drawing Sheets

PROCESS FOR THE CONTINUOUS PREPARATION OF MONO- AND/OR BIS (MONO-AND/OR DI-AND/OR TRICHLOROMETHYL) BENZENES

FIELD OF THE INVENTION

The present invention relates to a continuous process for the preparation of mono- and/or bis(mono- and/or di- and/or trichloromethyl)benzenes.

BACKGROUND OF THE INVENTION

Mono- and/or bis (mono- and/or di- and/or trichloromethyl)benzenes are important intermediates in the preparation of pesticides, colorants, herbicides and additives for plastics (UV stabilizers).

The usual technique for obtaining these chlorinated intermediates consists in carrying out the chemically or photochemically initiated chlorination of the methylbenzenes.

This reaction is generally carried out industrially with chlorine gas. As this reaction is that of a gas with a liquid, the overall kinetics of the reaction are controlled both by the chemical kinetics and the physical kinetics, that is to say the diffusion of the chlorine gas. The chemical kinetics depend essentially on the nature of the substituent or substituents on the benzene as well as on the initiation method.

The mechanism of the reaction is that of a radical chain reaction, the yield decreasing sharply between the various stages of the chlorination, that is to say from the starting —$CH_3$ to the monochlorinated compound —$CH_2Cl$, then to the dichlorinated compound —$CHCl_2$ and finally to the trichlorinated compound —$CCl_3$.

Consequently, towards the and of the reaction, when the content of hydrogen atoms on the —$CH_3$ capable of being substituted is relatively low, side reactions, such as chlorination on the ring, can take place.

In particular, these side reactions will increase in importance as the amount of available chlorine increases and when a sufficient amount of the radical species is no longer present.

In order to mitigate these disadvantages, provision is made, in Patent Application FR 2,156,911, relating to the preparation of trichloromethylbenzene, to dilute the excess chlorine with an inert gas, such as nitrogen, in order to decrease the undesirable side reactions.

In addition, long residence times (contact times) are used in order to achieve complete chlorination of the underchlorinated intermediates However, the aforesaid way of operating exhibits the disadvantage that an excessively large amount of chlorine necessarily passes into the effluents, with the inert gas, which necessitates continuous treatment operations on the said effluents: if desired, to recover the gaseous hydrochloric acid produced during the reaction; or destruction operations; or, as in the abovementioned application, the use of a second chlorination plant, in as much as in FR 2,156,911, the photochemical chlorination of toluene is carried out in a cascade of reactors divided into two sections.

In a first section composed of 5 reactors, 2.3 to 2.9 mol of chlorine per mole of toluene are injected, i.e. 86 to 96% of the amount of chlorine theoretically necessary to prepare trichloromethylbenzene.

Subsequently, the mixture obtained is chlorinated in the second section, composed of 4 reactors, with an excess of chlorine diluted with an inert gas.

The effluents from the final reactors pass into the first reactor of the first section. The chlorine content in the exiting HCl is less than 1%.

In the second section, the final reactor has a volume which represents 2 to 3 times the volume of all the preceding reactors of the two sections.

However, this system does not make it possible to eliminate the by-products sufficiently, since the final product comprises approximately 5% of ring-chlorinated by-products.

Another known system is described in U.S. Pat. No. 4,056,455 of a continuous process for the photochlorination of toluene which consists in carrying out the reaction in a cascade of 10 reactors.

The toluene is introduced into the first reactor, the reactors 2 to 9 being fed with predetermined amounts of chlorine gas.

The effluents from the reactors 5 to 10, which are rich in chlorine, return to the reactors 2 and 3.

Likewise, the effluents from the reactors 2 to 4 are introduced into the reactor 1 comprising a high concentration of toluene, so that a large part of the chlorine present in the HCl in converted.

However, with this process, it is found that the gaseous hydrochloric acid still comprises a significant amount by weight of chlorine, which is still at most equal to 2%.

This amount of chlorine necessarily results in the chlorination on the ring of the methylbenzenes entrained when scrubbing out hydrochloric acid with water. This results in a poor quality of the hydrochloric acid solutions as it is difficult to remove the methylchlorobenzenes (heavy products) by stripping and virtually impossible to recycle the phase in which they are present.

Furthermore, it is found, in FIG. 1 of the patent in which the plant is shown diagrammatically, that the 10 reactors are represented in the same way. Consequently, there is nothing which could allow it to be supposed that the said reactors would be different in size.

Furthermore, it is generally accepted that oxygen has an effect on radical reactions, in particular on chlorination reactions of aromatic or aliphatic organic compounds, it being possible for this effect to be favourable or unfavourable to the progression of the reaction.

Thus, Serguchev Jv. A. et al. (Zhurnal org. khim, (1983) XIX, Vol. 5, pages 1020–1023) studied the action of oxygen on the rate of radical chlorination of the side chain of toluene.

They showed that, by carrying out the reaction with carefully deoxygenated toluene at temperatures of between 90° C. and 130° C. and by using chlorine with an $O_2$ content in the region of 0.02% by volume, the chlorination of toluene to trichloromethylbenzene was carried out with a yield of 95% after 26 hours in the absence of chemical initiators and of light radiation.

SUMMARY OF THE INVENTION

A continuous process as now been found for the preparation of mono- and/or bis(mono- and/or di- and/or trichloromethyl)benzenes, optionally substituted on the benzene ring by one or more halogen atoms, by gradual chlorination of the corresponding mono- or dimethylbenzenes in several (at least two) reactors in cascade, characterized in that the volume of the first reactor is greater than the volume of each of the other reactors and in that all the waste gases from the other reactors are conveyed to the said first reactor.

According to the present invention, the reaction is carried out under light irradiation at a temperature of between 50° C. and 180° C. and preferably of between 75° C. and 145° C.

The reaction is also carried out in the presence of an amount of oxygen at most equal to 50 vpm and preferably at moot equal to 20 vpm in the gases (chlorine plus HCl).

According to the present invention, the mono- or dimethylbenzenes introduced into the first reactor are deoxygenated beforehand by azeotropic drying or (preferably) by stripping with the gaseous effluents, predominantly composed of the hydrogen chloride formed, exiting from the said first reactor.

The volume of the first reactor is greater than the volume of the other reactor or reactors.

The chlorine gas is purified by conventional means known to a person skilled in the art, such as degassing. Use can also preferably be made of re-evaporated chlorine originating from a manufacturing process resulting in a chlorine comprising very little oxygen, such as the so-called membrane electrolysis process.

According to the present invention, it is preferred that the volume of the first reactor is 1.1, 1.2, 1.3, 1.4 or more preferably 1.5 times to 2 times the volume of the second reactor, and when there are more than 2 reactors, 1.1 . . . 2.4 and more preferably 2.5 times to 3 times the volume of the third reactor and 1.1 . . . 7.9, more preferably 8 to 10 times the volume of each of the other reactors. (The ellipsis in both cases is intended as short hand for all intermediate values.)

According to the present invention, the number of reactors varies to a large extent and depends in particular on the desired degree of chlorination and on the specifications required for the finished products.

If it is desired to obtain mono- or bis(trichloromethyl) benzenes, use will be made of a number of reactors at least equal to 5 and preferably equal to 6. In this configuration, all the reactors are fed with fresh chlorine, except for the first.

If the case where it is desired to obtain mono- or bis (mono- or dichloromethyl)benzenes, use will be made of 2, or indeed even 3, reactors. In this configuration, all the reactors can be fed with fresh chlorine gas.

According to the present invention, use is made, as source of light irradiation, of mercury vapour lamps with a power of between 1 and 15 kW and preferably of between 3 and 10 kW.

The number of these lamps per reactor can vary to a large extent. It depends on the power desired. This number can range from 1 to 5 per reactor. These lamps are preferably immersed in the reaction mixture.

According to the present invention, the first reactor or reactors are conventional reactors, optionally comprising baffles, which are stirred by the gas stream. The following and final reactors are preferably reactors of plug-flow type.

The reactors are equipped-with at least one axial lamp which is supported at the top part and which passes through virtually the whole of the reactor. The liquid and the chlorine are introduced into the bottom part and rise towards the top part of the reactor, from where they are extracted.

The heat of reaction given off by the chlorination can be removed from the reactors by any known means, such as a continuous stream of cold water circulating in the jacket or else by an exchanger situated inside or outside the reactors or else by evaporation of the most volatile compounds.

Generally, the reaction is preferably carried out at atmospheric pressure. Higher or lower pressures can be used but generally do not confer any substantial improvement on the process. A pressure will preferably be chosen so that the chlorine is always in the gaseous form at the temperatures used in each reactor.

According to the present invention, the temperatures, which are identical or different for each reactor, are between 50° C. and 180° C. and preferably between 75°C. and 145°C.

According to the present invention, the liquid chlorination reaction mixture advantageously passes from one reactor to another by gravity and is conveyed, after the final reactor, into a storage tank.

The waste gases from all the reactors, with the exception of the first reactor, comprising hydrogen chloride formed, unreacted chlorine and optionally entrained chlorinated products, are introduced into the first reactor.

Hydrochloric acid exits from this first reactor with a chlorine content by weight generally of less than 0.2%.

The chlorine/compound to be chlorinated molar ratio depends on the desired chlorinated product(s), Thus, this ratio is equal to approximately 3/1 when it is desired to obtain trichloromethylbenzene.

In the case where it is desired to obtain preferably dichloromethylbenzenes, this ratio will be greater than 2/1 and preferably between 2.01/1 and 2.05/1.

In the case where it is desired to obtain a mixture of mono- and dichloromethylbenzenes, this ratio will vary to a large extent and will depend on the amounts of mono- and dichloromeethylbenzenes desired.

In the case where the reaction products are solid, such as, for example, 1,4-bis(trichloromethyl)-benzene, use may be made of light inert solvents preferably chosen from the group of fluorinated or chlorinated solvents. Mention will be made, as illustration of such solvents, of carbon tetrachloride, chloroform or 1,4-chlorotrifluoromethylbenzene.

Thus, if it is desired to obtain a mixture rich in benzyl chloride, the reaction will advantageously be carried out with a chlorine to toluene molar ratio of between 0.4 and 0.6.

Mention will be made, as illustration of mono- or dimethylbenzenes which can be used according to the present invention, of toluene, chlorotoluenes, fluorotoluenes, 2,4- and 2,6-dichlorotoluenes, xylenes and the mixture of at least two of the abovementioned compounds.

The process applies very particularly to toluene, to xylenes and to para-chlorotoluene.

This process exhibits the advantage of resulting in a high yield of mono- and/or bis(mono- and/or di- and/or trichloromethyl)benzenes.

In addition, the HCl obtained has a chlorine content by weight $\leq 0.2\%$.

This process also exhibits great flexibility since, by varying the number of reactors, it is possible to produce mono- or bis(trichloromethyl)-benzenes or else mono- or bis (mono- and/or dichloromethly)benzenes.

The examples which follow illustrate the invention.

EXAMPLE 1

Preparation of trichloromethylbenzene by chlorination of toluene.

Figure 1:
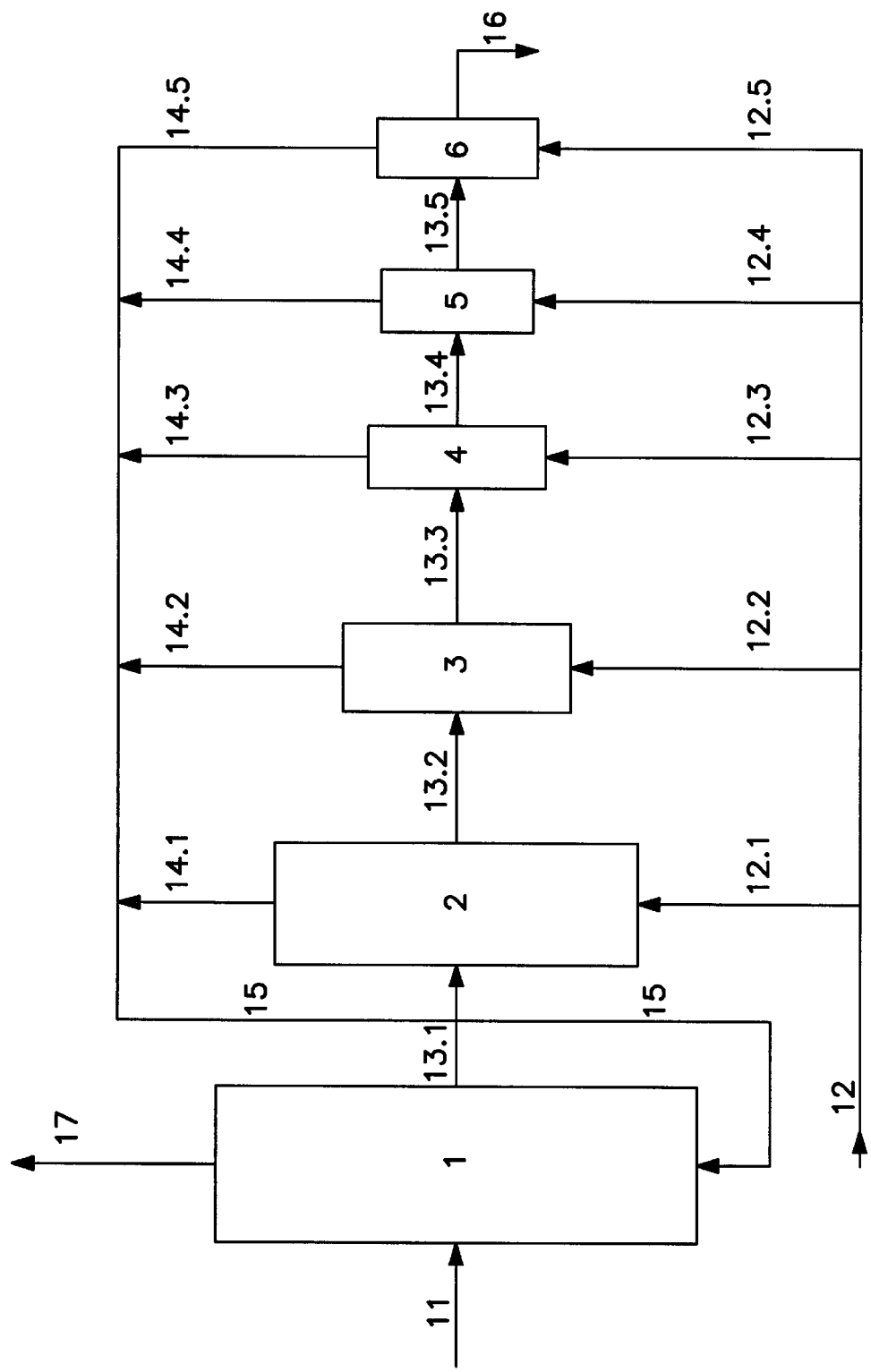
FIG. 1 is a block flowsheet of a plant containing 6 reactors, as further explained in Example 1.

Use is made of a plant comprising 6 enamelled reactors in cascade, an represented in FIG. 1, the said reactors being equipped with mercury vapour lamps immersed in the reaction mixture (theme lamps not being represented in FIG. 1).

The volumes of the reactors, the number of lamps per reactor and the power of these lamps are shown in Table 1. In this plant, 6.82 kilomol of toluene and 20.7 kilomol of fresh chlorine are reacted continuously per hour, which corresponds to a chlorine to toluene molar ratio equal to 3.03.

The temperatures of each reactor are recorded in Table 1.

Fresh chlorine is introduced into the reactors 2 to 6 respectively via the pipes 12.1, 12.21 12.3, 12.4 and 12.5 at hourly flow rates as shown in Table 1.

The toluene, deoxygenated beforehand and with an oxygen content of less than 5 mg/kg, is conveyed to the reactor 1 via the pipe 11 at a flow rate of 627.44 kg/h and then passes by gravity through the reactors 2 to 6, respectively via the pipes 13.1, 13.2, 13.3, 13.4 and 13.5, while forming $C_6H_5CCl_3$.

TABLE 1

| REACTOR | VOLUME ($m^3$) | MERCURY VAPOUR LAMP | | TEMPE- RATURE (° C.) | FEED OF | |
|---|---|---|---|---|---|---|
| | | NUMBER PER REACTOR | POWER OF EACH LAMP (W) | | TOLUENE (kg/h) | FREE CHLORINE (kg/h) |
| 1 | 2.5 | 3 | 4 | 96.1 | 627.44 | — |
| 2 | 1.5 | 3 | 4 | 151.8 | — | 783.7 |
| 3 | 1 | 3 | 4 | 135.9 | — | 392.9 |
| 4 | 0.3 | 1 | 8 | 144.3 | — | 224.9 |
| 5 | 0.3 | 1 | 8 | 143.5 | — | 57.9 |
| 6 | 0.3 | 1 | 8 | 138.1 | — | 11.1 |

1335.48 kg of trichloromethylbenzene are obtained per hour via the pipe 16.

The flow rate for feeding the reactor 1 with toluene and the flow rate for feeding the reactors 2 to 6 with fresh chlorine are also shown in Table 1.

The waste gases exiting from the reactors 2 to 6, respectively via the pipes 14.1, 14.2, 14.3, 14.4 and 14.5, are collected in the pipe 15 and are introduced into the reactor 1. These waste gases entering the reactor 1 comprise amounts by weight of HCl gas and of unreacted chlorine equal to approximately 40% and approximately 13%, respectively. They also comprise unconverted toluene (approximately 8% and entrained mono-, di- and trichloromethylbenzenes.

The composition by weight of the liquid reaction products exiting from each reactor has been shown in Table 2. In this table: Y1 represents chloromethylbenzene, Y2 represents dichloro-methylbenzene and Y3 represents trichloromethylbenzene.

"Heavy products" denotes products chlorinated on the ring.

The hydrogen chloride exiting from the reactor 1 via the pipe 17 has a chlorine content by weight of less than 0.2%.

The trichloramethylbenzene obtained has a purity of 97.7%; the content by weight of dichloromethylbenzene is 0.11%, the remainder of the by-products being composed essentially of trichloromethylbenzenes chlorinated on the ring or chlorinated by addition to double bonds, as well as coupling products with two aromatic rings.

TABLE 2

COMPOSITION OF THE LIQUID PRODUCTS EXITING FROM EACH REACTOR (WEIGHT %)

| REACTOR | TOLUENE | Y1 | Y2 | Y3 | HEAVY PRODUCTS |
|---|---|---|---|---|---|
| 1 | 38.23 | 23.11 | 16.22 | 20.54 | 0.16 |
| 2 | 2.3 | 17.78 | 41.71 | 36.72 | 0.28 |
| 3 | 0.03 | 2.15 | 27.60 | 68.95 | 0.61 |
| 4 | 0.01 | 0.75 | 11.99 | 86.05 | 0.56 |
| 5 | — | — | 0.73 | 97.36 | 0.93 |
| 6 | — | — | 0.11 | 97.74 | 1.22 |

EXAMPLE 2

Preparation of chloromethylbenzene and of dichloromethylbenzene.

Figure 2:
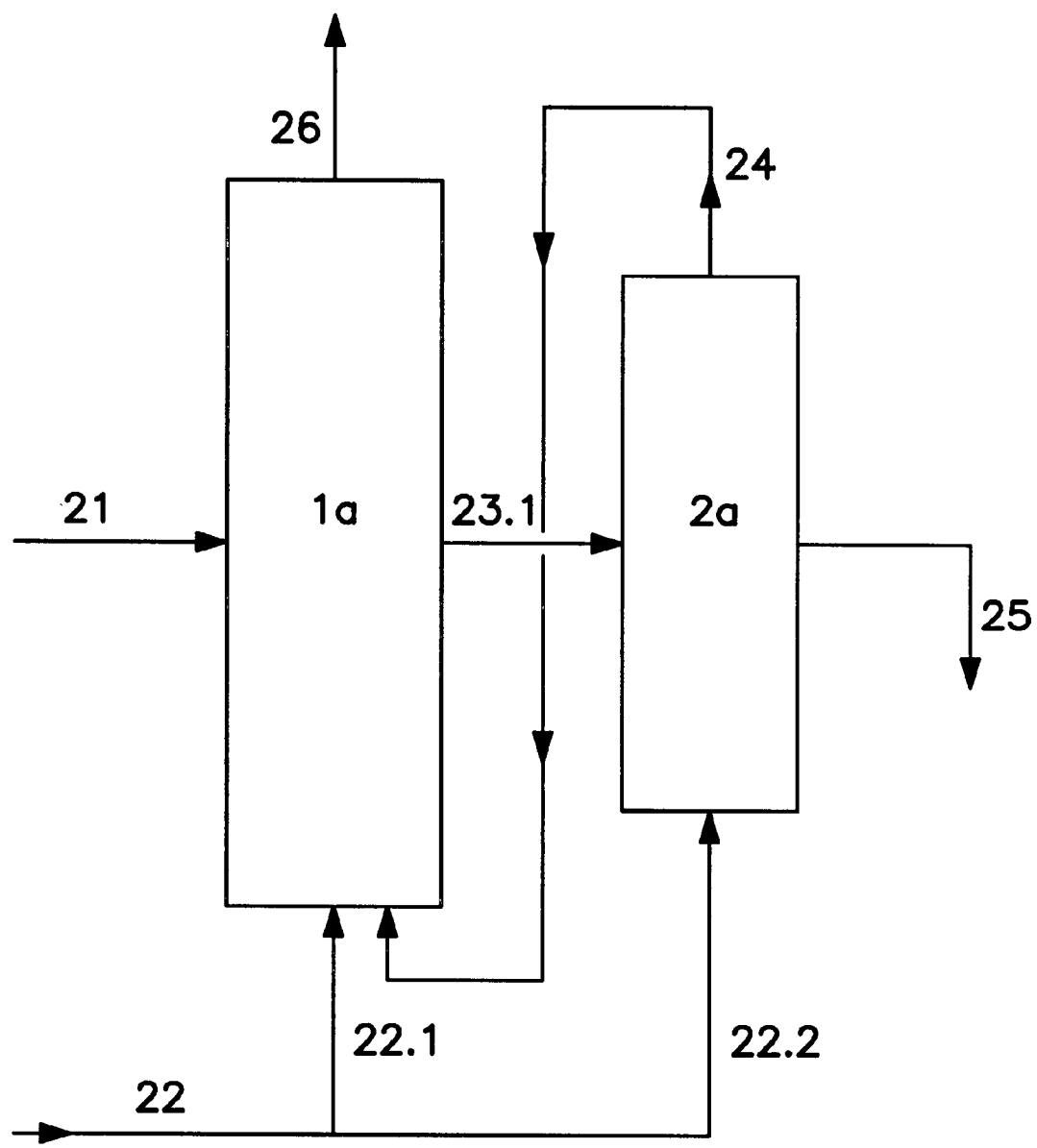
FIG. 2 is a block flowsheet of a plant containing 2 reactors as further explained in Example 2.

Use is made of a plant comprising 2 enamelled reactors in cascade, as represented in FIG. 2, the said reactors being equipped with mercury vapour lamps immersed in the reaction mixture (these lamps not being represented in FIG. 2). The volumes of the two reactors, the number of lamps per reactor and the power of these lamps are shown in Table 3.

In this plant, 33.15 kilomol of toluene and 18.31 kilomol of fresh chlorine are reacted continuously per hour, which corresponds to a fresh chlorine to toluene molar ratio equal to 0.55.

The temperatures of the two reactors are shown in Table 3.

Fresh chlorine is introduced into the reactors 1a and 2a respectively via the pipes 22.1 and 22.2 at hourly flow rates as shown in Table 3.

The toluene, deoxygenated beforehand and with an oxygen content equal to approximately 3 mg/kg, is conveyed to the reactor 1a via the pipe 21 at a flow rate of 3050 kg/h and then enters the reactor 2a by gravity via the pipe 23.1, while forming a mixture of $C_6H_5CH_2Cl$ and $C_6H_5CHCl_2$.

3681.7 kg of a mixture comprising, by weight, 51.93% of chloromethylbenzene, 6.78% of dichloromethylbenzene and 41.12% of unconverted toluene are obtained per hour via the pipe 25. This mixture is subsequently subjected to fractional distillation under reduced pressure.

TABLE 3

| Reactor | Volume (m³) | Mercury vapour lamp | | Temperature (° C.) | Feed of fresh chlorine (kg/h) |
| --- | --- | --- | --- | --- | --- |
| | | Number per reactor | Power of each lamp (W) | | |
| 1a | 2.5 | 3 | 4 | 100 | 767.1 |
| 2a | 1.5 | 3 | 4 | 116.6 | 533.5 |

The waste gases exiting from the reactor 2a via the pipe 24 are introduced into the reactor 1a. These gases comprise amounts by weight of HCl gas and of unreacted chlorine equal to approximately 42% and less than 1%, respectively.

The composition by weight of the liquid reaction products exiting from each reactor has been shown in Table 4.

In this table, Y1 represents chloromethylbenzene, Y2 represents dichloromethylbenzenes and Y3 represents trichloromethylbenzene.

TABLE 4

| | COMPOSITION OF THE LIQUID PRODUCTS EXITING FROM EACH REACTOR (% BY WEIGHT) | | | |
| --- | --- | --- | --- | --- |
| REACTOR | Toluene | Y1 | Y2 | Y3 |
| 1a | 61.84 | 35.09 | 3. | 0.05 |
| 2a | 41.12 | 51.93 | 6.78 | 0.17 |

The hydrogen chloride exiting from the reactor 1a via the pipe 26 has a chlorine content by weight of less than 0.2%.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/04460, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a continuous process for the preparation of mono- and/or bis- benzenes, optionally substituted on the benzene ring by at least one of monochloromethyl, dichloromethyl and/or trichloromethyl and/or one or more halogen atoms, comprising gradually chlorinating a feed of corresponding mono- or dimethylbenzenes in a plurality of reactors in cascade, said feed being first chlorinated in a first reactor and the resultant product from the first reactor being chlorinated in at least one other reactor, the improvement wherein the volume of the first reactor is greater than the volume of each of the other reactor or reactors and wherein all waste gases exiting from the other reactor or reactors are conveyed to the said first reactor.

2. A process according to claim 1, wherein chlorination is carried out under light irradiation.

3. A process according to claim 2 wherein a source of light irradiation is at least one mercury vapor lamp per reactor each having a power between 1 and 15 kW.

4. A process according to claim 1 wherein the chlorination is carried out at a temperature of between 50° C. and 180° C.

5. A process according to claim 1 wherein the chlorination is carried out in the presence of an amount of oxygen at most equal to 50 vpm.

6. A process according to claim 5 wherein the chlorination is carried out in 2 reactors in cascade.

7. A process according to claim 1 wherein the volume of the first reactor is 1.5 times to 2 times the volume of the second reactor, and if more than 2 reactors, 2.5 to 3 times the volume of the third reactor and 8 to 10 times the volume of each of the other reactors.

8. A process according to claim 1 wherein the chlorination is carried out in 6 reactors in cascade.

9. A process according to claim 8, wherein the chlorination is carried out by introducing fresh chlorine into the reactors, with the exception of the first reactor.

10. A process according to claim 1 wherein the chlorination is carried out in 2 reactors.

11. Process according to claim 10, wherein the chlorination is carried out by introducing fresh chlorine into the 2 reactors.

12. A process according to claim 1 wherein the chlorination is carried out in 5 reactors in a cascade.

13. A process according to claim 1 wherein the chlorination is carried out in 3 reactors in cascade.

14. A process according to claim 1 wherein the first reactor comprises baffles and the final reactor is a plug-flow reactor.

15. A process according to claim 1 wherein a stream exiting the first reactor comprises hydrochloric acid with a chlorine content by weight generally less than 0.2%.

16. A process according to claim 1, wherein the process comprises more than two reactors.

* * * * *